US00PP07912P

United States Patent [19]

van Andel

[11] Patent Number: Plant 7,912

[45] Date of Patent: Jul. 14, 1992

[54] CARNATION NAMED STABARSTRO

[75] Inventor: Jacob van Andel, Aalsmeer, Netherlands

[73] Assignee: Van Staaveren B.V., Aalsmeer, Netherlands

[21] Appl. No.: 583,947

[22] Filed: Sep. 13, 1990

[51] Int. Cl.[5] ..... A01H 5/00

[52] U.S. Cl. ..... Plt./70.5

[58] Field of Search ..... Plt./70, 71, 72

[56] References Cited

U.S. PATENT DOCUMENTS

P.P. 3,591 8/1974 Barberet et al. ..... Plt. 70

*Primary Examiner*—Howard J. Locker

*Attorney, Agent, or Firm*—Charles W. Rummler

[57] ABSTRACT

A new and original mini-spray carnation variety particularly distinguished by its small, pink-colored blossoms, which are borne in a tight, umbel-like cluster and are produced intermittently during the Spring, Summer, and Fall blooming periods. The bush-shaped plant has a vigorous and upright growth habit and reaches a height of about 60 cm.

1 Drawing Sheet

BACKGROUND OF THE NEW PLANT

This new mini-spray carnation cultivar originated as a sport of the variety 'Stadia', discovered by me in 1986 at our nursery in Aalsmeer; Holland. This particular sport was selected for propagation because of its unusual rose-flecked light pink flower coloration and the overall high quality of the plant. Asexual propagation of this selected plant was done by means of cuttings under my direction at Aalsmeer; and propagation of this new plant by cuttings was continued from generation to generation to determine whether the novel characteristics of this sport would be retained from generation to generation and its homogeneity could be assured.

This proved to be successful and this new mini-spray carnation variety is now being propagated at Aalsmeer.

DESCRIPTION OF THE DRAWING

My new mini-spray carnation cultivar is illustrated by the accompanying photographic drawing, which shows blooming portions of spray stems with both buds and flowers, the color rendition being as nearly true to that herein specified as is reasonably possible to obtain by professional photographic procedures.

DESCRIPTION OF THE NEW PLANT

The following is a detailed description of my new mini-spray carnation cultivar based upon observation of plants grown in greenhouse as well as outdoors at Aalsmeer and blooming during the current year. The color designations stated herein are according to the R.H.S. Colour Chart published by The Royal Horticultural Society of London, England.

THE PLANT

Origin: Sport.

Parentage: Stadia. (U.S. Plant Pat. No. 7,802).

Classification:

*Botanic.*—Dianthus Hybrid.

*Commercial.*—Mini-spray carnation.

Form: Strong, upright bush with hardly any shoots in the flower stem nodes.

Height: 60 cm, in average.

Main stem:

*Length.*—In average, about 50 cm.

*Growth.*—Vigorous and erect.

*Branching character.*—Hardly any shoots in the flower stem nodes.

Foliage:

*Number of leaves.*—Abundant, varying with season.

*Leaf size.*—About 130 mm long and 12 mm wide at the fifth node.

*Leaf shape.*—Long, elliptical and slightly curled. Margins: Entire. Texture: Leathery. Color: Both upper and under sides are dark green.

THE BUD

Size: Small.

*Diameter.*—Averaging about 7 mm.

*Length.*—Averaging about 20 mm.

Shape: Cylindrical.

Calyx:

*Shape.*—Oblong.

*Size.*—Averaging about 8 mm in width and 20 mm in length.

*Splitting.*—The calyx does not split.

*Aspect.*—Smooth.

THE FLOWER

Blooming habit: Intermittent, during Spring to Fall blooming seasons.

Size of flower: Small.

*Diameter.*—Averaging about 30 mm.

*Depth.*—Averaging about 10 mm.

Borne: In a close, umbel-like cluster.

Shape when first opening: Flat.

*When mature.*—Become somewhat rounded.

Petalage:

*Number of petals.*—About 25 to 30 in average.

*Texture.*—Soft.

*Color.*—Upper sides: Both outer petals and inside petals: Body: 62 C/D with some marks of 61 B. Base: White. Reverse Side: 62 C/D.

Flower stem:

*Length.*—Averaging about 50 cm.

*Color.*—Dark green.

*Character.*—Erect and strong.

Discoloration:

*After full bloom.*—None.

Persistence: The flowers hang on and dry.

Disease resistance: Highly resistant to *Fusarium oxysporum.*

Fragrance: Normal.

Lasting quality: Averaging about 14 days as a cut flower and 21 days on the plant.

REPRODUCTIVE ORGANS

Stamens:

*Number.*—Few.

*Arrangement.*—Rudimental.

*Anthers.*—Size: Small. Color: Beige.

*Filaments.*—Length: Averaging 20 mm. Color: White.

*Pollen.*—Color: Beige, if present.

Pistils:

*Number.*—1.

*Styles.*—Length: About 25 mm. Color: White.

Stigmas:

*Color.*—Pink.

This presently claimed plant can be distinguished from Stadia (U.S. Plant Pat. No. 7,802) by the light pink colored petals as compared to Stadia's deep crimson colored petals. Further distinguishing characteristics include the calyx shape which is oblong for this plant and cylindrical for Stadia.

This presently claimed plant can be distinguished from the cited reference U.S. Plant Pat. No. 3,591 on the following grounds. The presently claimed plant has a different leaf size; 130 mm. long and 12 mm. wide versus the leaves of U.S. Plant Pat. No. 3,591 which are 11 cm. (110 mm.) long and 1.2 cm. (12 mm.) wide. Thus, the present plant's leaves are longer. Furthermore, the leaves of the present plant are described as long, elliptical and slightly curved whereas the leaves of U.S. Plant Pat. No. 3,519 are described as short lanceolate and rarely curved. The flower size of the two plants also varies.

The flowers of the present plant are smaller—diameter 30 mm. and depth 10 mm. versus U.S. Plant Pat. No. 3,591 diameter 5.1 cm. (51 mm.) and depth 2.3 cm. (23 mm.). The colors of the flower petals also serve to distinguish between the two plants. The present plant is R.H.S. 62C and D with stripes of 61B. U.S. Plant Pat. No. 3,591 is 65B and C with stripes of 61A.

I claim:

1. The new and distinctive mini-spray carnation plant, substantially as herein shown and described, particularly characterized by the pink coloration of its flowers, which are flecked with stripes of red, its vigorous growth habit and the intermittent and profuse production of flowers on its strong, upright stems.

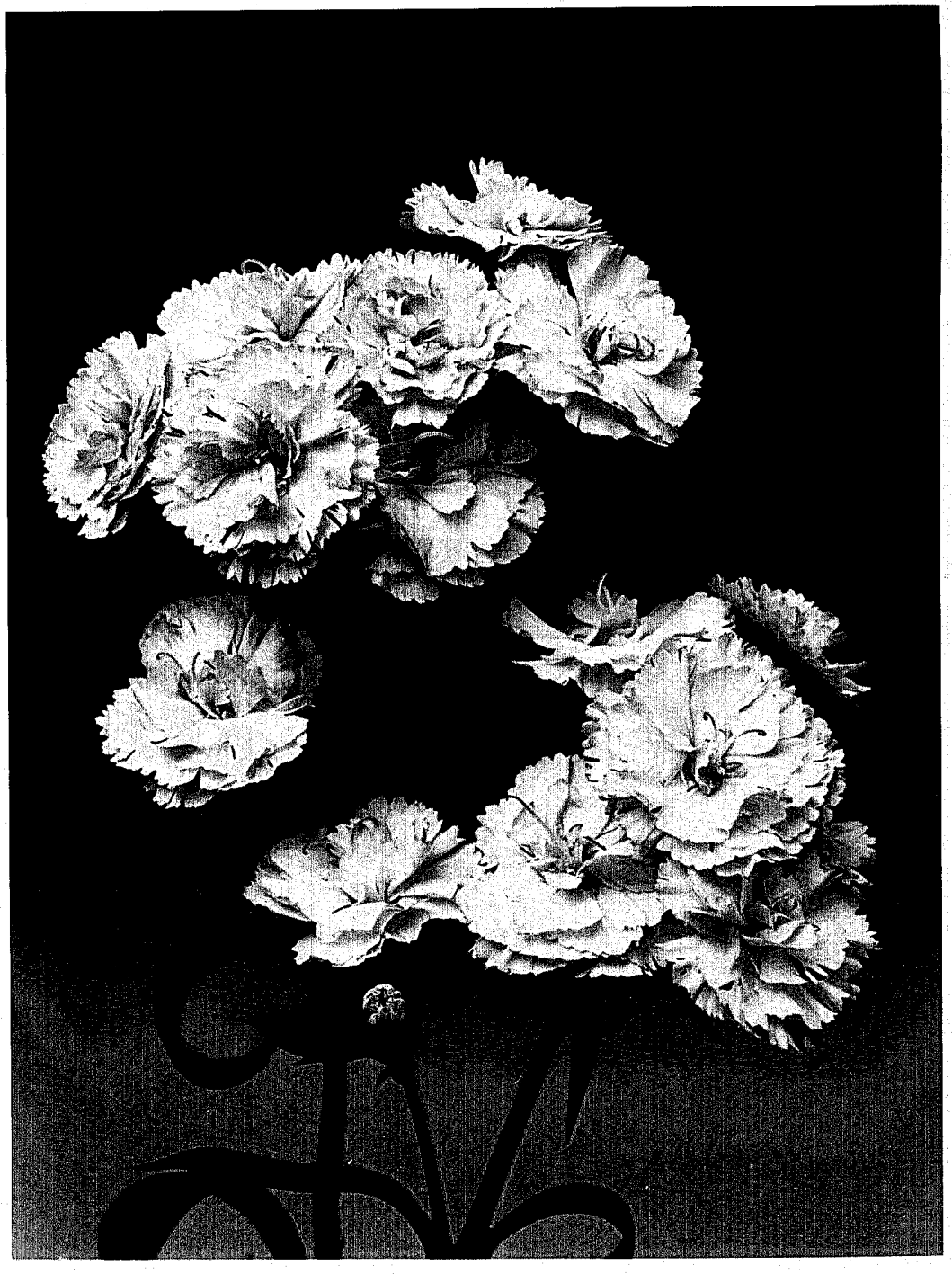

* * * * *